United States Patent
Duffy, Jr. et al.

(10) Patent No.: US 8,048,678 B2
(45) Date of Patent: Nov. 1, 2011

(54) CELL SEPARATION METHOD AND APPARATUS

(75) Inventors: Neil F. Duffy, Jr., Brighton, MA (US); Jeffrey R. Chabot, Medford, MA (US); Edward H Kislauskis, Medway, MA (US)

(73) Assignee: ECW Therapeutics, Inc., Marshfield, MA (US)

( * ) Notice: Subject to any disclaimer, the term of this patent is extended or adjusted under 35 U.S.C. 154(b) by 0 days.

(21) Appl. No.: 12/826,074

(22) Filed: Jun. 29, 2010

(65) Prior Publication Data

US 2011/0033925 A1 Feb. 10, 2011

Related U.S. Application Data

(63) Continuation of application No. 11/588,835, filed on Oct. 27, 2006, now abandoned.

(60) Provisional application No. 60/731,058, filed on Oct. 27, 2005.

(51) Int. Cl.
C02F 1/02 (2006.01)
(52) U.S. Cl. .......... 436/70; 436/177; 435/325; 600/580; 210/513; 422/58; 422/918; 422/939
(58) Field of Classification Search .............. 422/58, 422/918, 939–949; 222/94–107; 210/513–540; 600/580; 436/70, 177; 435/325
See application file for complete search history.

(56) References Cited

U.S. PATENT DOCUMENTS

| | | | | | |
|---|---|---|---|---|---|
| 3,441,205 | A | * | 4/1969 | Young, Jr. | 53/431 |
| 3,513,976 | A | * | 5/1970 | James | 210/782 |
| 3,911,918 | A | * | 10/1975 | Turner | 604/410 |
| 3,965,889 | A | * | 6/1976 | Sachs | 600/577 |
| 4,040,959 | A | * | 8/1977 | Berman et al. | 210/782 |
| 4,187,861 | A | * | 2/1980 | Heffernan | 600/577 |
| 4,266,559 | A | * | 5/1981 | Akhavi | 600/579 |
| 4,511,349 | A | * | 4/1985 | Nielsen et al. | 494/16 |

(Continued)

FOREIGN PATENT DOCUMENTS

EP 0 493 838 A1 7/1992

(Continued)

OTHER PUBLICATIONS

International Preliminary Report on Patentability from counterpart International Application No. PCT/US2006/042237, dated May 8, 2008.

(Continued)

Primary Examiner — Brian R Gordon
Assistant Examiner — Shogo Sasaki
(74) Attorney, Agent, or Firm — Hamilton, Brook, Smith & Reynolds, PC

(57) ABSTRACT

Disclosed herein are apparatus and methods for isolating a fraction of interest from a physiological fluid sample. A sample holder for isolating a fraction of interest from a physiological fluid sample includes a flexible compartment and a rigid exoskeleton that supports the flexible compartment. The flexible compartment may have at least one reservoir with a height to volume ratio of about 0.1 cm/mL to about 5 cm/mL. An automated device for extracting a fraction of interest from the sample includes a sample holder with a flexible compartment supported by a rigid exoskeleton, a support for the sample holder connected to one or more fluid extraction devices, and a motor for moving the extraction device relative to the sample holder. The automated device may include an optical sensor and may include a clamp for clamping the flexible compartment.

18 Claims, 10 Drawing Sheets

U.S. PATENT DOCUMENTS

| | | | | |
|---|---|---|---|---|
| 4,617,009 | A | * | 10/1986 | Ohlin et al. .................. 494/21 |
| 4,663,032 | A | * | 5/1987 | Loos et al. .................. 210/97 |
| 5,030,215 | A | * | 7/1991 | Morse et al. .................. 604/410 |
| 6,019,716 | A | | 2/2000 | Forestell et al. |
| 6,516,953 | B1 | * | 2/2003 | DiCesare et al. .......... 210/516 |
| 7,179,391 | B2 | | 2/2007 | Leach et al. |
| 7,223,346 | B2 | | 5/2007 | Dorian et al. |
| 7,337,907 | B2 | * | 3/2008 | Shah .......................... 206/570 |
| 7,374,678 | B2 | | 5/2008 | Leach et al. |
| 2002/0006360 | A1 | * | 1/2002 | Neal et al. .................. 422/100 |
| 2002/0052008 | A1 | * | 5/2002 | Mahant et al. ............... 435/7.2 |
| 2003/0205538 | A1 | | 11/2003 | Dorian et al. |
| 2004/0217069 | A1 | * | 11/2004 | Columbus .................. 210/782 |
| 2006/0273049 | A1 | | 12/2006 | Leach et al. |
| 2006/0273050 | A1 | | 12/2006 | Higgins et al. |
| 2007/0265558 | A1 | | 11/2007 | Kleinbloesem et al. |
| 2008/0171951 | A1 | | 7/2008 | Fell |

FOREIGN PATENT DOCUMENTS

| | | |
|---|---|---|
| WO | WO 00/60351 | 10/2000 |

OTHER PUBLICATIONS

Notification of Transmittal of the International Search Report and Written Opinion of the International Searching Authority from counterpart International Application No. PCT/US2006/042237, dated Mar. 23, 2007.

Juopperi, T. A., et al., "Isolation of Bone Marrow-Derived Stem Cells Using Density-Gradient Separation," *Exp. Hematol.*, 35: 335-341 (2007).

Thermogenesis Res-Q™ 60 BMC, "Bone Marrow Concentrate, Laboratory Point of Care," 2 pages retrieved May 4, 2010 from http://www.thermogenesis.com/CMSFiles/Pdf/Literature/resqbmc.pdf.

Totipotent SC "RES-Q60 BMC, Point-of Care Automated Cell Capturing System," 6 pages retrieved Nov. 24, 2010 from http//www.totipotentsc.com/products/RES-60M_V2.pdf.

Zhang, B., et al., "Isolating and Culturing Rat Marrow Mesenchymal Stem Cells and Studying their Phenotypical and Functional Properties," *Sichuan Da Xue Xue Bao Yi Xue Ban*, 34(4):738-741 (2003).

* cited by examiner

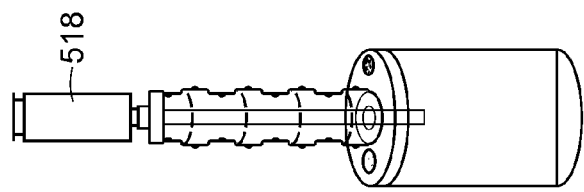
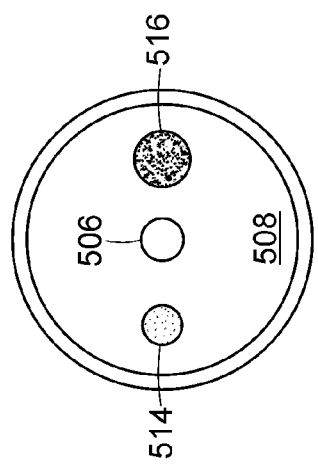
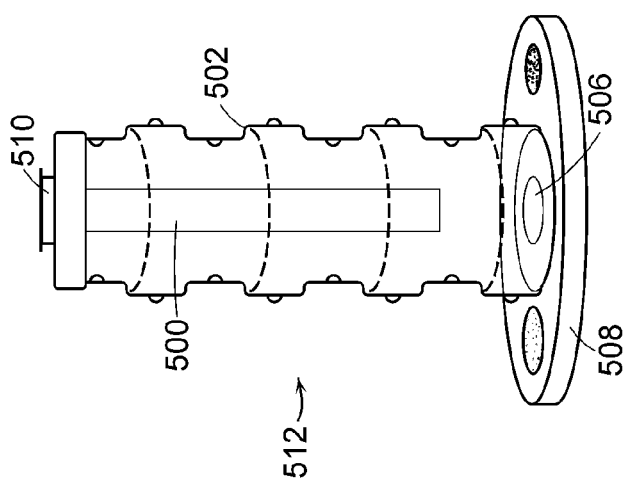

_US 8,048,678 B2_

CELL SEPARATION METHOD AND APPARATUS

RELATED APPLICATION

This application is a continuation of U.S. application Ser. No. 11/588,835, filed Oct. 27, 2006, which is now abandoned, and which claims the benefit of U.S. Provisional Application No. 60/731,058, filed on Oct. 27, 2005. The entire teachings of the above application are incorporated herein by reference.

BACKGROUND OF THE INVENTION

Separating blood components for transfusion or intra-operative red blood cell ("RBC") salvage has been a standard practice of medicine for the last 50 years. These procedures generally involve relatively large volumes of blood, and in the case of blood banking are usually not for autologous use. Additionally, laboratories have been separating blood proteins for diagnostic testing for years. Improved methods for fractionating blood samples have allowed for better separation of factions.

Smaller blood separation devices have been introduced into the market for concentrating, for example, platelets from a small volume of blood. These devices allow for improved concentration of, for example, the growth factors in platelets that can be applied topically or injected locally to patients. These devices typically rely upon an apheresis method or a rigid plastic disposable device with density shelves for separating components of relatively small volumes of blood.

Increasingly, the therapeutic potential of stem cells is being recognized for many clinical applications including, for example, regenerative therapy. Certain early pioneers of stem cell technology used blood banking equipment designed for transfusion medicine or small volume platelet concentration systems to concentrate stem cells at point of care from marrow or umbilical cord blood. Both of these methods present the practitioner with varying problems such as the large volume of marrow aspirate required, varying volumes of umbilical blood processed, and low percent yields in the ending concentrate.

Stem cells are found in specific blood samples, two rich sources of stem cells being umbilical cord blood and bone marrow. During fractionation by sedimentation, stem cells in these samples typically migrate in a small volume known as the "buffy coat" fraction. The buffy coat fraction appears as a small volume density layer after sedimentation. Because mononuclear cells and stem cells present in the buffy coat represent such a small percentage of the overall volume of cord blood and marrow, and because clinical applications using stem cells require highly concentrated buffy coat fractions, there is a well-demonstrated and increasing need to capture and concentrate a high percentage of these cells into a small volume.

SUMMARY OF THE INVENTION

The current invention is designed to meet the emerging need to concentrate stem cells from a physiological fluid sample, e.g., bone marrow aspirate or umbilical cord blood. The apparatus and methods herein allow for a greatly increased recovery and concentration of fractionated layers, with a method that is conveniently adapted to point of care use. The apparatus and methods allow for recovery of the buffy coat fraction in a much smaller volume than, for example, the blood banking industry, the diagnostic device industry, and presently available point of care platelet concentrating devices. The apparatus and methods allow for, in addition to highly efficient and concentrated recovery of the buffy coat, convenient isolation of platelet poor plasma ("PPP") and red blood cell ("RBC") fractions. The apparatus and methods allow for the partial or complete automation of the collection and separation of stem cells from umbilical cord blood or bone marrow aspirate or platelets from blood, while maintaining the ability to recover PPP and RBC fractions. In particular, the apparatus and methods enable the recovery of these fractions under sterile conditions.

One method is a method of isolating a fraction of interest from a physiological sample, comprising placing a physiological fluid sample comprising a plurality of cells in a container comprising a flexible compartment supported by a rigid exoskeleton; separating the plurality of cells into distinct relative density layers; isolating cells in the flexible compartment by clamping the flexible compartment; and extracting a desired fraction. The exoskeleton can comprise additional compartments at one or both ends of the flexible compartment and the volume of the exoskeleton compartments is selected to have the selected fraction of interest sediment in the flexible compartment. For example, the flexible compartment can have a height to volume ratio that is between about 2 to about 10 times greater than the exoskeleton compartments or a height to volume ratio greater than about 10 times the exoskeleton compartments. In another example, the flexible compartment comprises an upper reservoir and a lower reservoir. The lower reservoir can have a height to volume ratio that is about 2 to 10 times greater than the height to volume ratio of the upper reservoir, about 3 to 4 times greater than the height to volume ratio of the upper reservoir, or about 3.4 times greater than the height to volume ratio of the upper reservoir.

The methods can be used for physiological fluid samples that are, for example, blood samples (e.g., the blood sample is obtained from bone marrow aspirate or umbilical cord blood). For blood samples, the desired fraction to be isolated can be, for example, the buffy coat fraction. In addition, the methods can allow for the isolation of more than one fraction of interest from the sample, for example, the isolation of the buffy coat fraction, platelet poor plasma, red blood cells, or combinations thereof.

The methods can be performed under sterile conditions at point of care. Devices used for extracting fractions of interest, for example, can be sterilized in a sheath that protects the extraction device from exposure to non-sterile environments after sterilization. For example, the extracting step can comprise inserting a cannula into the exoskeleton through the top of the exoskeleton, accessing the flexible compartment, and withdrawing a fraction volume through the cannula. The fraction volume is a predetermined volume above the clamp. The cannula can be enclosed in a sheath, allowing for the cannula to be sterilized and used without exposing the cannula to a non-sterile environment.

The method allows for the volumes of the flexible compartment and exoskeleton to vary for different physiological samples; for example, samples obtained from male and female patients can exhibit different relative fraction volumes, and different species may only be able to provide samples of different (e.g., limited) volume. The methods can allow for the different sample volumes obtained from these and other sample sources.

The method comprises determining the volume of the compartments to isolate the fraction of interest in a relatively narrow region of the flexible compartment. Once fractionated, the fraction of interest can be isolated with a clamp below the fraction of interest and/or a clamp above the fraction of interest. The methods and apparatus can be designed to fit commercially available centrifuge tubes or rotors, and the exoskeleton can withstand g forces associated with centrifugation. The extraction of fractionated samples can be performed by an automated device.

Another method is for preparing platelet rich plasma at point-of-care, comprising placing a blood sample in a flexible container; supporting the flexible container with a rigid exoskeleton; allowing the sample to form a density gradient by sedimentation; clamping the flexible container below the buffy coat fraction; and extracting a volume of platelet poor plasma from above the buffy coat fraction. This method also allows for the isolation of the buffy coat layer. This method can also comprise clamping the flexible container above the buffy coat layer. Sedimentation can be achieved by centrifugation.

Another method is for preparing concentrated mononuclear cells from bone marrow aspirate or umbilical cord blood at point of care, comprising placing an umbilical cord blood sample or bone marrow aspirate sample in a flexible container; supporting the flexible container with a rigid exoskeleton; allowing the sample to form a density gradient by sedimentation; clamping the flexible container below the buffy coat fraction; removing platelet poor plasma with a cannula, leaving the buffy coat fraction intact; and extracting the buffy coat fraction from the flexible container. This method can also comprise clamping the flexible container above the buffy coat layer. This method can be performed wherein the centrifugation and/or clamping and/or removing steps are performed within one or more automated hardware devices.

An apparatus can include a physiological fluid sample holder for isolating a fraction of interest comprising a flexible compartment comprising at least one reservoir with a height to volume ratio about 0.1 cm/mL to about 5 cm/mL; and a rigid exoskeleton that supports the flexible rigid compartment.

An automated device for extracting a desired fraction of interest from a physiological sample can comprise a sample holder comprising a flexible compartment supported by a rigid exoskeleton; a support for the sample holder; a syringe connected to a cannula; and a motor for moving the cannula relative to the sample holder. The automated device can comprise an optical sensor. The automated device can comprise a clamp for clamping the flexible compartment of the sample holder.

A method of isolating a fraction of interest from a physiological sample, can comprise placing a physiological fluid sample comprising a plurality of cells in a container comprising a flexible compartment supported by a rigid exoskeleton and a cap comprising an access port, tube and sheath enclosing the tube; separating the plurality of cells into distinct relative density layers; isolating cells in the flexible compartment by clamping the flexible compartment; accessing the flexible compartment by inserting the tube through the access port; and extracting the fraction of interest. The cap, tube, sheath and container are sterilized prior to placing the sample in the container. A cap assembly structure is used with the sheath protecting the tube from an outside, non-sterile environment.

BRIEF DESCRIPTION OF THE DRAWINGS

FIGS. 6A-D show apparatus used for the sterile transfer, fractionation and extraction of a physiological sample.

DETAILED DESCRIPTION OF THE INVENTION

Figure 1A:
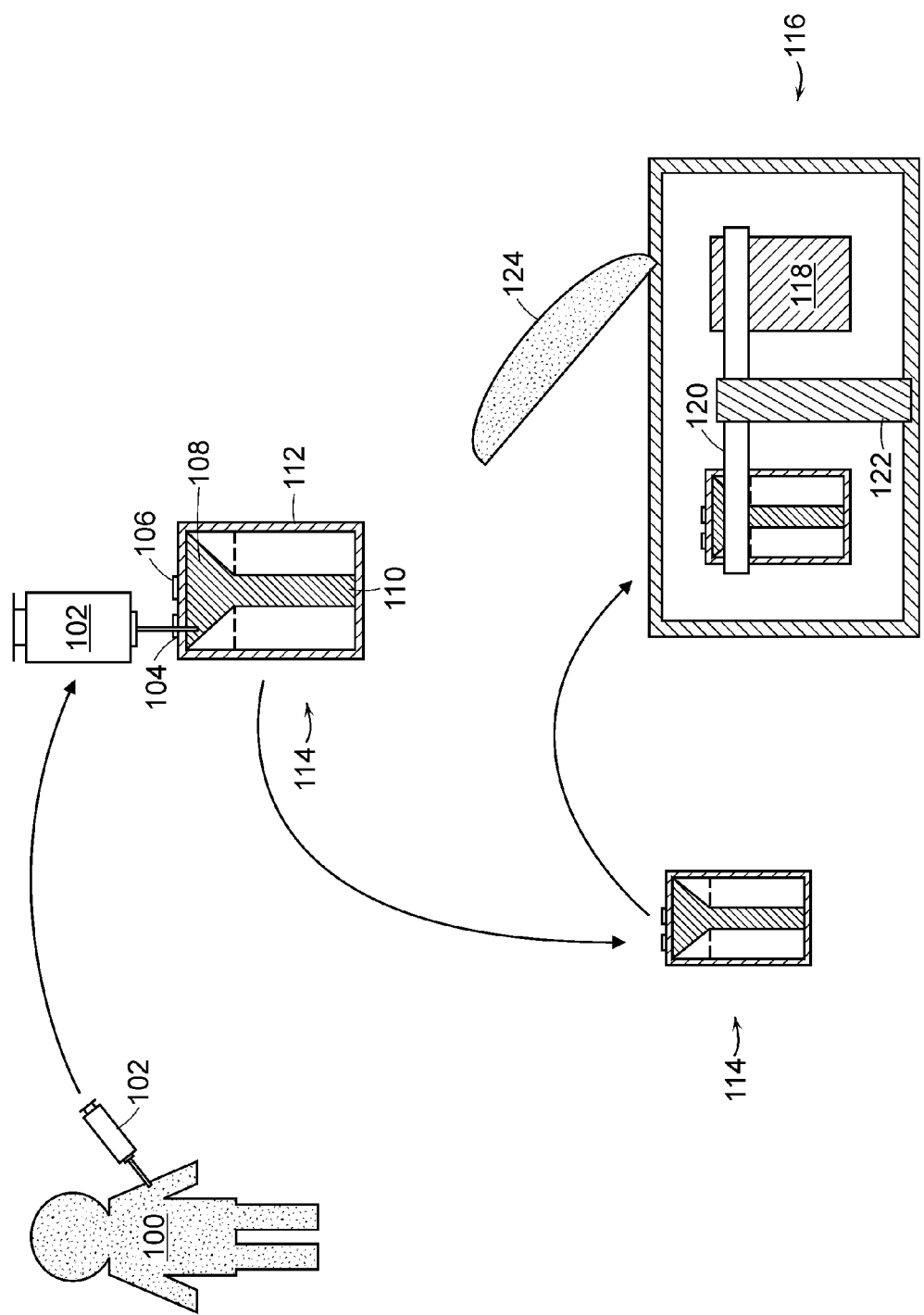
FIGS. 1A-E are diagrams depicting the steps of a blood/marrow fractionation method.

A description of example embodiments of the invention follows.

Described herein are improved methods and apparatus for isolating fractions from physiological fluid samples. There is presently a need to obtain increased yields and higher concentrations of fractionated blood samples, for example. The methods, apparatus and kits described herein allow for increased yields and higher concentration of fractions, and they can be readily adapted to sterile conditions and point of care therapies. In particular, therapies based on "stem cells," pluripotent cells capable of differentiating into one or more differentiated cells, can be improved with a higher concentration of isolated stem cells (Eichler, H. et al., 2003, *Stem Cells*, 21:208-216; Hernigou, P. et al., 2005, *J. Bone Joint Surg.*, 87A:1430-1437; Schächinger, V. et al., 2006, *N. Engl. J. Med.*, 355:1210-1221; Lunde, K. et al., 2006, *N. Engl. J. Med.*, 355:1199-1209).

Whole blood is commonly separated into its major components by sedimentation, either by gravity with the addition of coagulants or by centrifugation. Cells are separated by relatively gentle centrifugation and sedimentation techniques so as not to disrupt the integrity of the cell. Centrifugation at high g-forces or ultracentrifugation will lyse the cells. Blood banks store fractionated samples for transfusion from donor to a recipient patient other than the donor. This process is contrasted with point of care therapies based on apheresis where a sample is fractionated and reintroduced back into the same patient. The amount of blood commonly processed by blood banks is usually in excess of 400 mL. The blood is most commonly separated into less dense plasma and more dense red blood cells (RBCs) by first drawing the whole blood into a plastic bag known as a donor or primary bag. The contents of the bag are then centrifuged under controlled conditions to result in a lower, more dense portion of packed RBCs and an upper less dense plasma portion. Although the plasma and RBC fractions are useful for some therapies, additional fractionation is required to derive a concentrated "buffy coat" fraction, and an improved procedure would be required for point of care therapies.

The classical method of preparing platelet transfusion products from whole blood collections consists of initial centrifugation of whole blood in a plastic blood bag at relatively low centrifugal force to separate most of the "platelet rich plasma" ("PRP") from the red cells. The PRP is commonly expressed into an attached satellite blood bag. This is followed by centrifugation of the PRP in the satellite bag at relatively high centrifugal force to form a lower sediment of platelets and an upper "platelet poor plasma" ("PPP"). The sedimented platelets are in the form of a pellet or "button" that is typically resuspended in a small volume (50-60 mL) of donor plasma to give the platelet concentrate. Other methods have been described to further fractionate and concentrate whole blood samples, however, these methods are either not suitable for point of care therapies, or provide low and diluted yields of pluripotent cells (U.S. Pat. Nos. 3,911,918; 4,608,178; 4,511,349). Methods currently available are typically either completely flexible, using bags, which make the integrity of the sedimentation (density) layers fragile, or they are rigid, which makes it difficult to recover high yields of pluripotent cells in a high concentration.

Whole blood samples, e.g., umbilical cord blood, peripheral blood and bone marrow aspirate, can readily be fractionated into plasma, buffy coat (containing mononuclear white blood cells and pluripotent progenitor cells), and packed RBCs. The plasma fraction can be separated into less dense PPP with the more dense platelets being part of the buffy coat fraction. Highly concentrated platelets in the buffy coat fraction are sometimes referred to as the "platelet gel." The apparatus, methods and kits described herein allow for the recovery of greater than about 75%, greater than about 80%, greater than about 85%, greater than about 90% or greater than about 95% recovery of the buffy coat fraction, often in volumes of less than about 1 mL, between about 1-2 mL, or less than about 3 mL. The isolation of the buffy coat fraction in this manner allows for recovery of other fractions as well, e.g., PPP and RBC fractions.

Platelets isolated by the methods and apparatus described herein offer advantages of current methods for isolating platelets. Platelets derived from platelet rich plasma, buffy coat and apheresis technologies differ in terms of in vitro functional activity, aggregation states and storage characteristics, as measured by automated cell counters, and pH assessment. Such disparities have been attributed to differences in the subpopulation of platelets and leukocytes recovered or the processing- and storage-induced cellular damage. In addition, some methods of platelet isolation appear to have a higher rate of bacterial contamination (Vasconselos, E. et al., 2003, *Transfus. Apher. Sci.*, 29:13-16). The apparatus and methods described herein allow for the isolation of platelets under sterile conditions and in a manner where point of care therapies are available, thereby reducing the risk for contamination and storage-induced cellular damage.

Use of the methods and apparatus described herein allows, for example, a surgeon to concentrate autologous stem cells at point of care from a fresh marrow harvest for clinical use. It also allows a surgeon to prepare an autologous platelet gel at point of care for clinical use. Additionally, use of the methods and apparatus described herein allows a doctor to capture umbilical cord blood in a sterile manner in the birthing room and ship that blood in a sterile manner to a blood bank. The blood bank can then use a centrifuge to harvest nearly all of the stem cells easily and efficiently in a small volume for storage.

The apparatus and methods described herein can be used and performed under conditions such that a sterile environment is maintained throughout the sample collection, sedimentation, fraction extraction, and reintroduction of a desired fraction into the patient (where applicable). For example, after sedimentation, e.g., by centrifugation, the closed apparatus can be clamped externally, and a sterilized closed cannula can be inserted into the sedimentation apparatus to extract the desired layer(s).

Figure 1B:
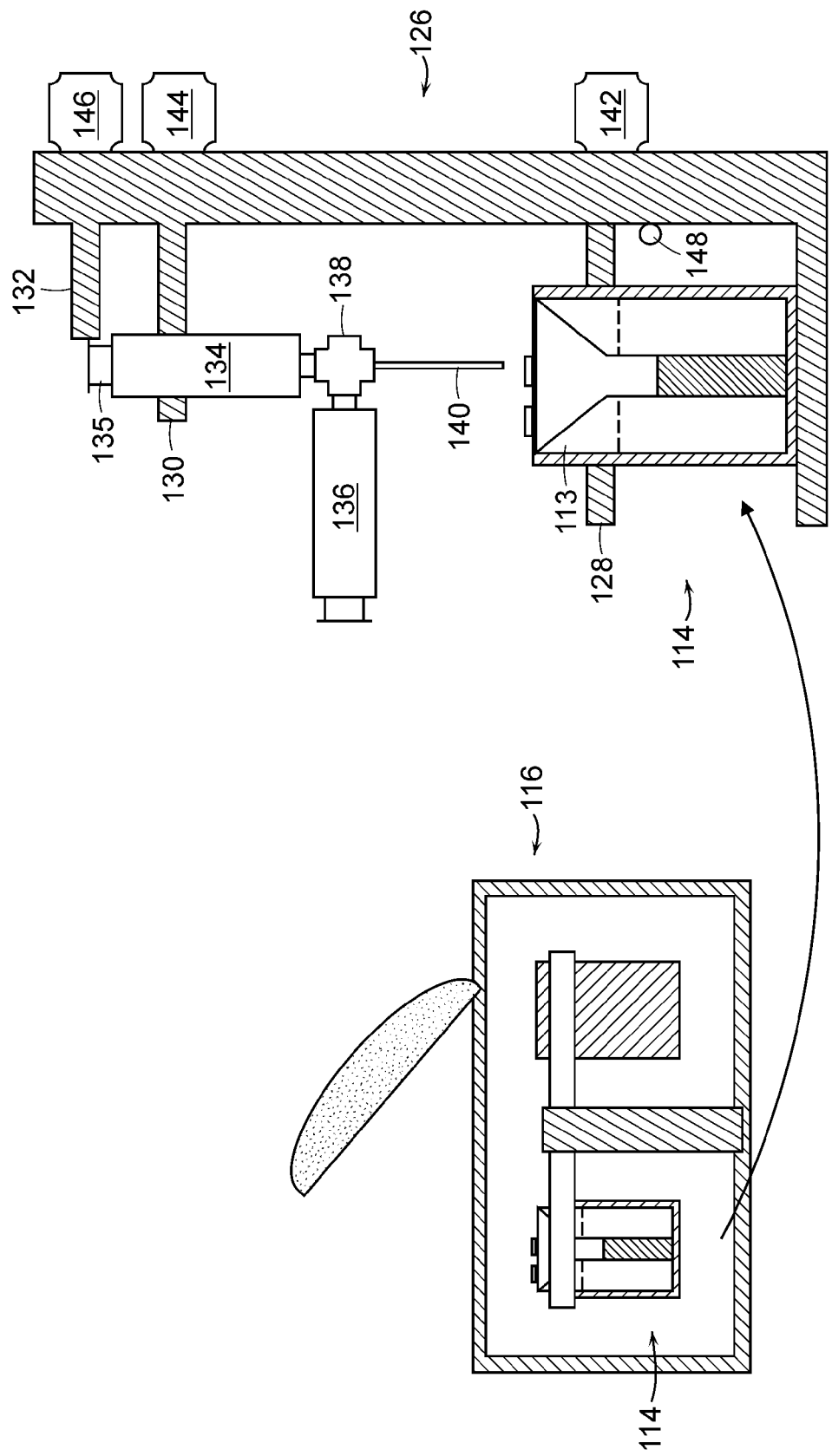

FIGS. 1A-E depict an embodiment of the methods and apparatus. The diagrams show obtaining a sample from a patient 100 with a syringe 102, and transfer of the sample though one of two sterile ports 104, 106 into a flexible compartment with an upper reservoir 108 and narrow, lower reservoir 110. The flexible compartment is supported by a rigid exoskeleton 112 to form the assembly 114. The assembly is then transferred to a centrifuge 116 comprising a counterbalance 118, swinging arm 120, rotor 122 and lid 124 (FIG. 1A). After centrifugation, the apparatus is transferred to an automated extraction device 126 comprising a movable assembly support arm 128 for the assembly 114, a syringe support 130 and movable plunger support arm 132, and two syringes 134, 136 joined by an adapter 138 connected to a cannula 140 (FIG. 1B). The assembly arm support 128 syringe support 130 and plunger support 132 are all movable vertically and driven by motors 142, 144, 146. An optical sensor 148 can also be present (FIG. 1B).

Figure 1C:
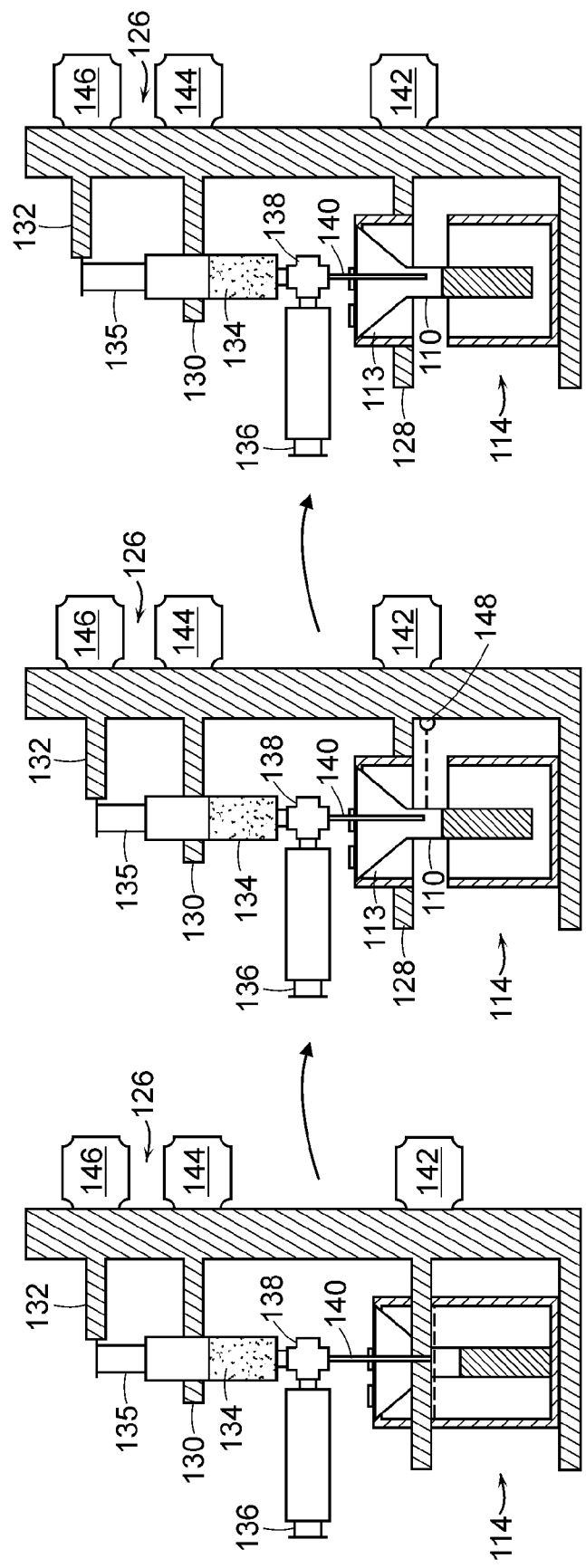
Figure 1D:
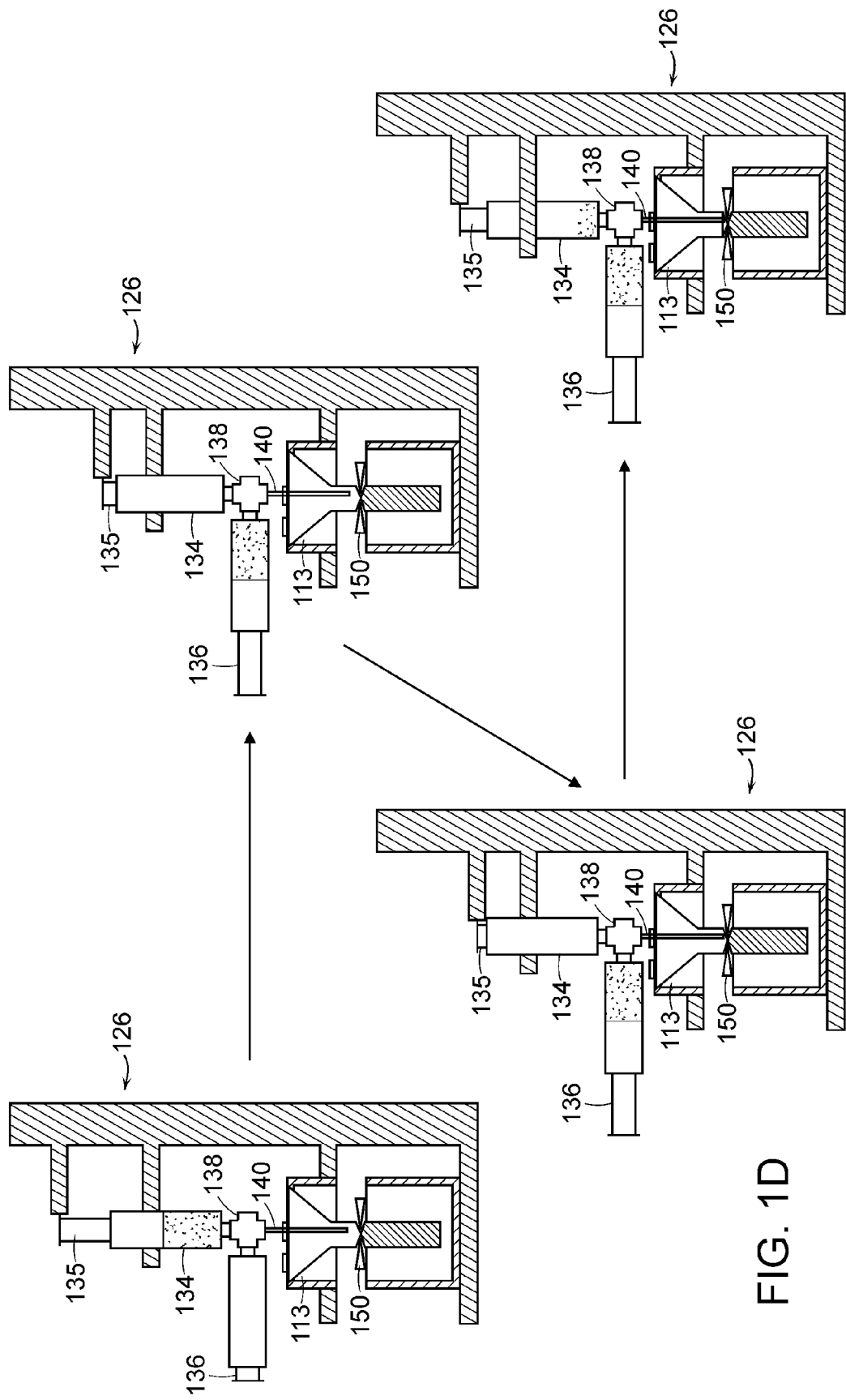
Figure 1E:
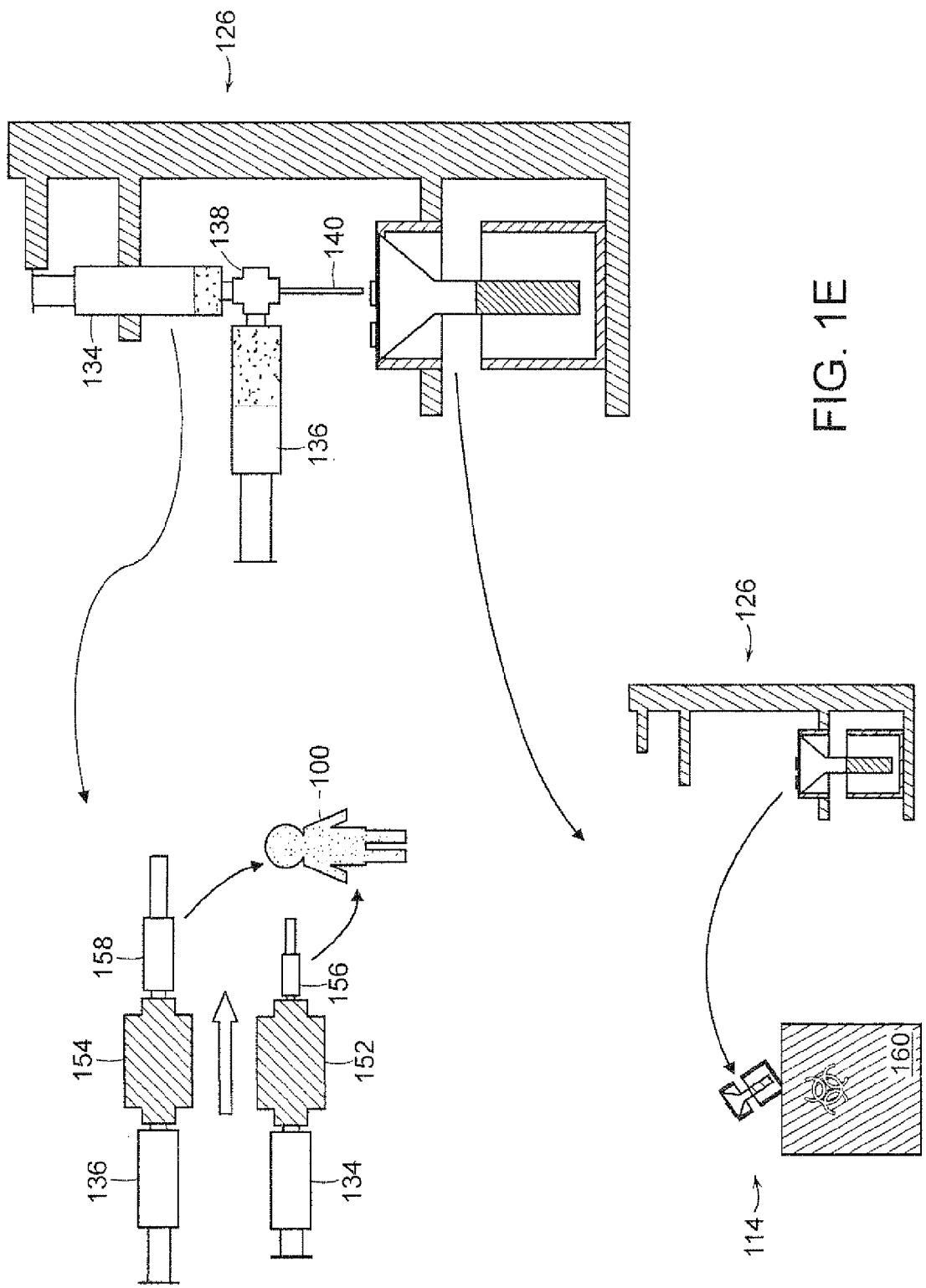

The syringe support motor 144 and plunger support motor 146 lower the cannula 140 into the assembly 114 to remove most of the plasma fraction (FIG. 1C, left panel). The plasma is removed as the plunger support motor 146 raises the plunger 135 of the syringe 134 relative to the syringe assembly 130. The assembly 114 is partially disassembled as the assembly support motor lifts the lid 113 of the exoskeleton 112 and thus the flexible compartment 110, thereby exposing the lower reservoir of the flexible compartment 110 (FIG. 1C, middle panel). An optical sensor 148 can be used to identify the buffy coat fraction, and the cannula 140 is again inserted to remove the rest of the plasma layer to a point just above the buffy coat (FIG. 1C, right panel). The flexible compartment 110 is then clamped 150 below the buffy coat, thereby restricting the flexible compartment and isolating the buffy coat fraction inside the flexible compartment (FIG. 1D, upper left panel). The extracted plasma is then directed to a side container 136 via the syringe adapter 138 by lowering the plunger 135 of the syringe (FIG. 1D, upper right panel). The cannula 140 is inserted to the base of the clamp 150 by lowering the syringe or cannula 140 or raising the lid 113 and flexible compartment 110 (FIG. 1D, lower left panel). The buffy coat layer is removed (FIG. 1D, lower right panel). The clamp 150 can then be removed from the flexible compartment 110. The syringe 136 now containing the plasma and the syringe 134 containing the buffy coat can be stored in a sterilized docking station 152, 154 where the plasma and buffy coat fractions are transferred to sterile syringes 156, 158. The plasma 158 and buffy coat 156 can then be reintroduced into a patient. The rest of the assembly 114 is disposed in an appropriate container 160 (FIG. 1E).

The apparatus 114 itself comprises a flexible compartment 108,100 and a rigid exoskeleton 112 that supports the flexible compartment 108,110. The exoskeleton 112 allows the flexible compartment 108,110 to maintain its shape during and after sedimentation, so as to not disturb the density layers formed during sedimentation. The flexibility of the flexible compartment 108,110 allows for it to be externally clamped, thereby internally isolating specific density layers. For example, after sedimentation, a clamp 150 can be externally applied to the flexible compartment 110 between the RBC and buffy coat layers. This clamping process can be performed in a way such that the buffy coat layer is not disturbed, e.g., does not mix with other layers. After clamping, the majority of the PPP fraction can be removed, followed by extraction of the buffy coat layer. Alternatively, the buffy coat layer can be clamped a second time above the buffy coat layer to prevent disruption of the buffy coat layer during extraction of the PPP and PRP fractions. The number of separate internal chambers that can be formed by clamping is limited only by the length of the constricted area of the flexible compartment 108,110.

Figure 2:
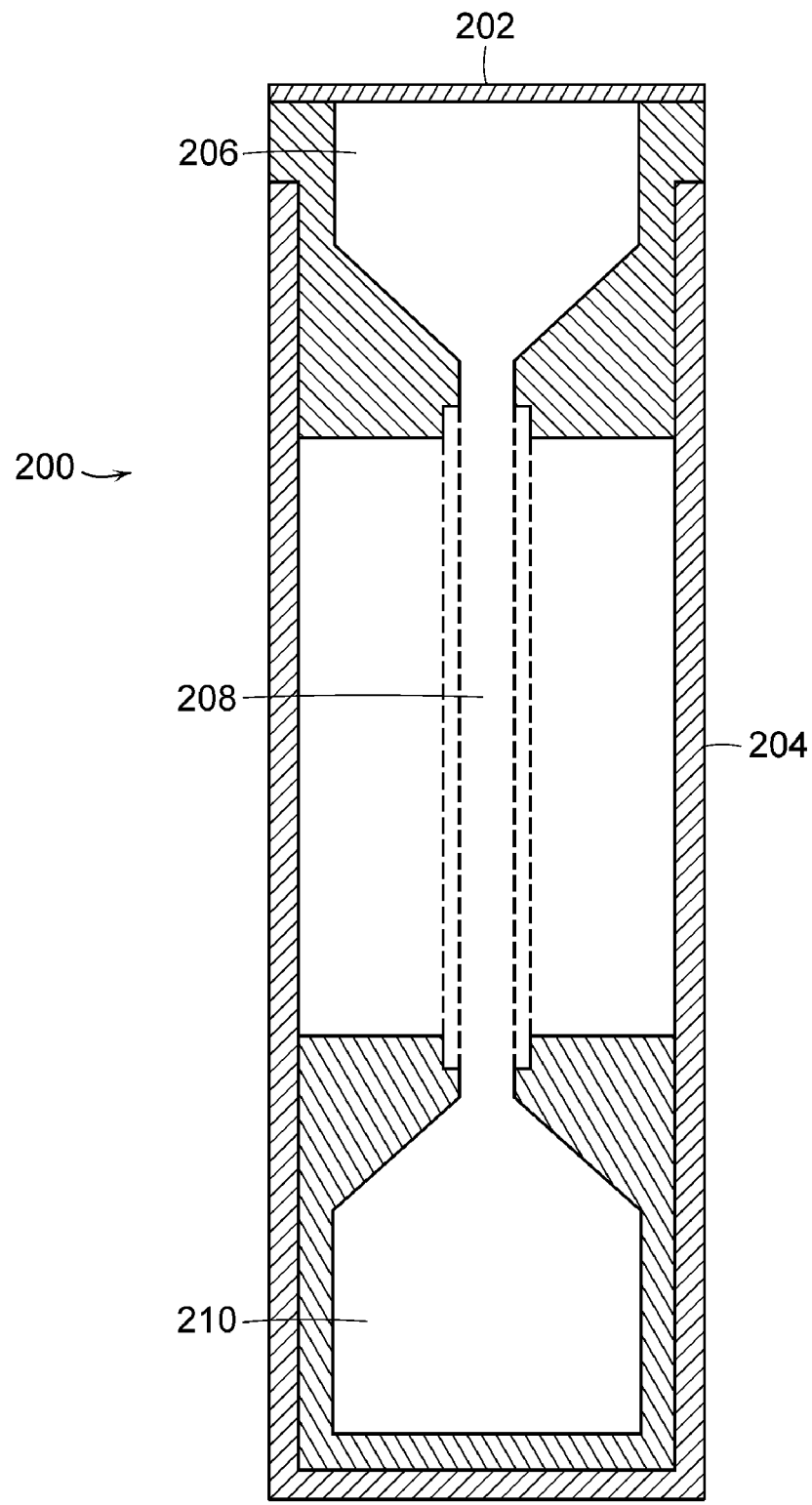
FIG. 2 is a schematic diagram showing one embodiment of the apparatus with a flexible compartment (see "Example 1").

FIG. 2 shows one embodiment of a physiological sample holder 200. A physiological fluid sample (e.g., peripheral blood, umbilical cord blood, or bone marrow, for example; of human or animal origin) is loaded into the sample holder via an injection port 202 at the top of the sample holder 200, and subjected to centrifugation. The top of the device can also include additional ports to maintain the integrity of the sample and extractions and to allow the passage of sterile, filtered air to prevent pressure differences while adding or removing samples or fractions. The sample holder has a rigid outer shell or exoskeleton 204, which can be solid or include holes and/or slots for accessing the contents. The exoskeleton 204 supports the inner structure of the disposable during centrifugation. The sample holder has an upper reservoir 206, constructed of rigid and/or flexible components, which will hold a significant fraction of the PPP, if the physiological fluid sample is a whole blood sample, for example. The bottom of this reservoir is tapered (nominally with a 90 degree included angle, but this can be varied to assist in the smooth flow of fluid components during centrifugation). The sample holder has a central section 208 of flexible tubing that mates smoothly with the upper 206 and lower reservoirs 210, again to allow for smooth fluid flow between these components. The volumes of the three reservoirs are determined such that, for example, if the sample is umbilical cord blood or bone marrow aspirate, the buffy coat fraction will sediment in the central reservoir 208. The flexible material that encases the central reservoir allow for isolation of the buffy coat by clamping. The lower reservoir, constructed of rigid and/or flexible components, and, as with the upper reservoir 206, the top is tapered for smooth fluid flow.

If the sample holder 200 is used to fractionate whole blood, three density layers form: platelet poor plasma (PPP), the buffy coat (containing white blood cells, stem cells, and other mononuclear cells), and a fraction of packed red blood cells (RBC). The specific volume fraction ranges for each of these components in the target fluid are used such that the PPP is contained principally within the upper reservoir 206 and extend slightly into the upper portion of the narrow central reservoir 208. The RBC is contained in the lower reservoir 210 and extend into the bottom of the narrow central reservoir 208. The buffy coat is contained specifically within the central part of the narrow central reservoir 208, regardless of the particular individual's RBC fraction (also known as the hematocrit (or "crit") level). The central reservoir 208 has a large height to volume ratio relative to the other reservoirs 206,210. This allows for a broader layer buffy coat layer, which is present in a relatively small volume compared to the whole blood sample. The broader buffy coat layer allows for easier processing, meaning a higher yield of buffy coat cells and/or a more concentrated buffy coat fraction.

Figure 3D:
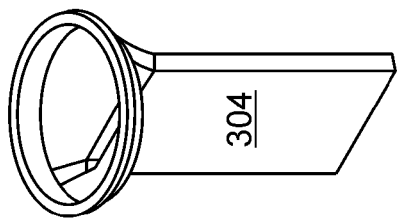
FIGS. 3A-3D are diagrams depicting another embodiment of the apparatus (see "Example 2"). The flexible compartment is shown as having a large upper reservoir and a flat lower reservoir, flat meaning the depth of the reservoir is substantially less than the width and height.

FIGS. 3A-3D show another embodiment of the apparatus. The flexible compartment 300 (FIGS. 3A and 3C) includes an upper reservoir 302 (FIG. 3B) and a flat lower reservoir 304 (FIG. 3D). The upper reservoir includes a flanged lip 306. The upper reservoir has a larger volume capacity and lower height:volume ("h/v") ratio. In one embodiment, the lower reservoir has a h/v ratio that is between about 3 to 4 times the h/v ratio of the upper reservoir. In another embodiment, the h/v ratio of the upper reservoir is about 2 to 10 times the ratio of the upper reservoir. In other embodiments, the h/v of the lower reservoir is greater than about 10 times the h/v of the upper reservoir. In a particular embodiment, the lower reservoir has a h/v ratio that is about 3.4 times the h/v ratio of the upper reservoir. As depicted, the height to volume ratio for the lower reservoir is 0.310 cm/mL, and the height to volume ratio of the upper reservoir is 0.090 cm/mL. The actual values of the h/v can be, for example, about 0.010 cm/mL to about 0.3 cm/mL for the upper reservoir, and about 0.1 cm/mL to about 5.0 cm/mL for the lower reservoir.

FIGS. 4A-4E show an exoskeleton 400 (FIGS. 4A-4E) designed to support a flexible compartment comprising a large volume upper reservoir and a flat lower reservoir. The lower reservoir fits into a narrow slit 404 (FIG. 4B) at the top of the exoskeleton. The upper reservoir of the flexible compartment fits into the cap assembly 402 of the exoskeleton. A flange 306 at the top of the flexible compartment abuts the top of the cap assembly.

Figure 5:
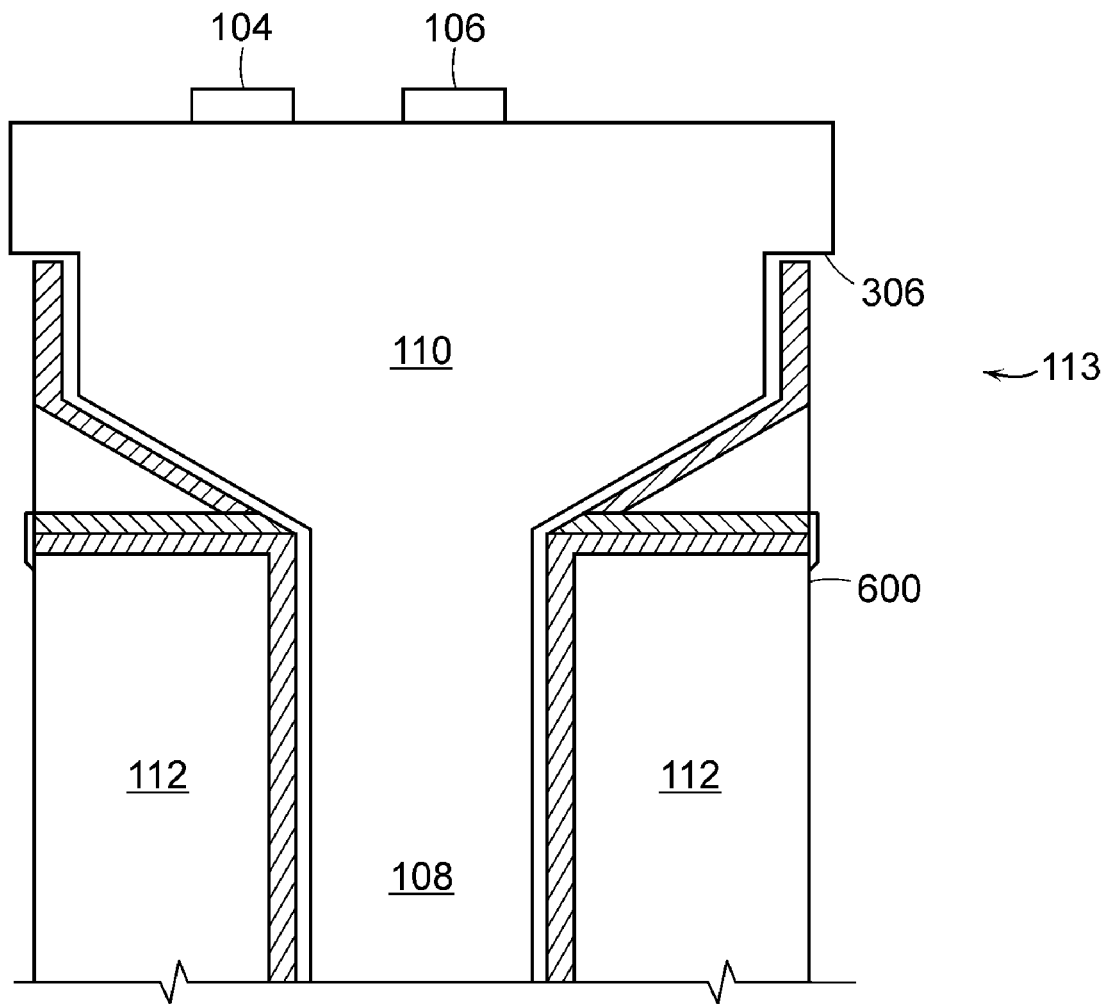
FIG. 5 shows an exoskeleton, flexible compartment and cap assembly.

FIG. 5 shows an exoskeleton 112, flexible container 108, 110 and cap assembly 113. The flanged lip 306 adjacent to the upper reservoir 110 abuts the top of the exoskeleton 112 when fully supported by the exoskeleton. The cap assembly 113, comprising ports 104,106 that allow access to the flexible compartment 108,110, fits onto the top of the exoskeleton 112 and is attached by an affixing mechanism (e.g., a threaded screw or clamping mechanism). The flanged lip 306 of the upper reservoir 110 fits between the top of the exoskeleton 112 and the cap assembly 113. The cap assembly 113 is affixed to the lower exoskeleton, for example, with an overhanging fastener 600.

The exoskeleton and flexible compartment assembly can be fit into an automated device that selectively removes specific density layers. The automated device can be equipped with an optical sensor that detects the boundaries of the different density layers. In one embodiment, the automated device comprises one or more cannulas that can be inserted into the exoskeleton and flexible compartment assembly. The process of "inserting" can be performed by moving the exoskeleton and flexible compartment assembly and cannula(s) relative to each other, e.g., by lowering the cannula(s) into the assembly held in a fixed position, by raising the assembly relative to the cannula(s) held in a fixed position, or by moving both the cannula(s) and the assembly. Alternatively, the cannula(s) can be inserted from the bottom of the exoskeleton.

The generalized method using the apparatus is depicted in FIGS. 1A-E. This figure is not intended to be limiting to one particular design of the flexible compartment, exoskeleton, or manner in which they are used.

EXEMPLIFICATION

Example 1

Hourglass-Shaped Apparatus

A blood sample obtained from a patient is transferred to a thin-wall centrifuge tube shaped generally like an hourglass (FIG. 2) and supported by an exoskeleton to create multiple chambers for use in fluid separation using low g-force centrifugation. More particularly, the hourglass-shaped tube can be used, for example, in concentrating stem cells and/or platelets from blood, e.g., bone marrow aspirate or umbilical cord blood. The hourglass-shaped tube can have several separate chambers along the constricted portion for more refined separation of materials. Subsequent to centrifugation, portions of the constricted non-rigid disposable can be accessed through cannulas from the top of the disposable or heat-sealed from each other to retain the separated cells to be used clinically. The entire non-rigid tube is a single, preferably injection-molded, unit that permits fluid communication. The tube is designed to be used in conjunction with an exoskeleton so that the top of the tube is properly supported by cleats during low g-force centrifugation. The exoskeleton is open at the top to allow the insert of the non-rigid device, which is secured to the exoskeleton by a thread and screw mechanism incorporated into the top of each component (exoskeleton and non-rigid disposable). For example, the exoskeleton can be open along two sides that are in line with the restricted portion of the flexible compartment to allow access by clamps or a sealing device.

In another example, the entire exoskeleton is to be solid. To access fluid in the constricted area, the flexible compartment can be removed from the exoskeleton to allow access to the constricted area of the flexible compartment by clamps or other sealing mechanism.

In view of the relative gradations of density between various cell types, low g-force centrifugation provides an obvious choice to accomplish the separation of various cells without damaging those cells. A physiological fluid sample placed into the flexible centrifuge tube can, during low g-force centrifugation, be supported by the exoskeleton, allowing for separation with the less dense material moving closest to the rotational axis of the rotor, while the denser material migrates farther from the spin axis of the rotor.

Volumes of the reservoirs in the flexible compartment and exoskeleton can be adjusted for sample size, differences in expected relative volumes of each fraction in the sample (e.g., varying hematocrit levels between males and females or between species, etc.). Various volume configurations of the constricted area are applicable. Additionally, in methods where the volume of fluid to be placed in the flexible compartment (e.g., a non-rigid disposable) is not known ahead of time (e.g., umbilical cord blood) a ratio of two inert fluids (volume expanding fluids) that are biocompatible with living cells (e.g., Ficoll gradient solutions) can be added to make up any volume shortfall. One of the two inert fluids should have a density greater than red blood cells and the other fluid should have a density less than blood plasma. These fluids are injected into the flexible compartment using a dual lumen syringe with each syringe preloaded with the inert materials. The ratio of the dispensing syringe should be such that the volume of expanding fluids is injected into the non-rigid disposable at the proper ratio with the denser solution matching the portion of blood made up of red blood cells and the less dense fluid matching the portion of blood made up of plasma. In the case of umbilical cord blood, where sterility is of utmost concern because the blood is eventually shipped to a blood bank, the exoskeleton containing the flexible compartment filled with umbilical cord blood can be fitted with a cap via a thread and screw mechanism to add additional sterility protection.

The hourglass-shaped centrifuge tube, supported by an exoskeleton for support, is manufactured based on the general range of red blood cell and plasma components contained in blood and/or marrow aspirate. Whole blood, marrow aspirate and umbilical cord blood generally contain plasma, red blood cells, white blood cells, other mononuclear cells, and platelets. The chosen relative volume for each of the upper and lower chambers of the hourglass-shaped tube is to ensure that after centrifugation the denser red blood cell fraction remain in the lower chamber, while the less dense plasma remain in the upper chamber. The buffy coat (containing platelets or concentrated mononuclear cells along with progenitor stem cells) remains in the middle flexible area of the tube.

Platelet rich plasma and/or concentrated mononuclear cells from bone marrow or umbilical cord blood is prepared by placing whole blood, umbilical cord blood or bone marrow aspirate in the reservoir of the sterile tube. The loaded tube is subjected to centrifugation to separate red blood cells, plasma and/or platelet rich plasma or concentrated mononuclear cells contained in the buffy coat. After centrifugation, the middle buffy coat is isolated by removing the tube from the exoskeleton or by accessing the constricted area of the tube through openings in the side of the exoskeleton and clamping the flexible compartment. The buffy coat containing platelet rich plasma or concentrated mononuclear cells is isolated with a clamping mechanism containing a top and bottom clamp either by sight or through an automated process using an optical reader. A volume of the platelet poor plasma supernatant above the upper clamp is removed. The upper clamp is then unfastened and the platelets or mononuclear cells are re-suspended in the remaining separated composition that was contained between the upper and lower clamps. The lower clamp separating the mononuclear cell or platelet concentration and the red blood cell layer is not removed until all material above it is previously removed as described above. Depending on the stability of the buffy coat during this process, it is in many cases possible to omit the upper clamp and individually or sequentially aspirate the platelet poor plasma and buffy coat fractions.

1) The ranges of separation forces for human blood are typically between 1200 and 1500 g; occasionally as low as 500 g. The nominal range can involve lower speeds when using animal blood samples, as such samples may sediment more readily.

2) Hematocrit ranges for various animals (for which the volume of the upper and lower reservoirs can be adjusted):
   a) Horses: 30%-50% (upper reservoir with 45% volume (for plasma), lower with 25% volume (for packed red blood cells))
   b) Dogs: 35%-55% (upper 40%, lower 30%)
   c) Cats: 25%-45% (upper 50%, lower 20%)

3) Crit ranges for peripheral blood in humans (including dehydrated people):
   Male: 40%-54%
   Female: 37%-48%
   Devices could be constructed using either of these ranges for gender-specific apparatus to cover all possibilities.
   In general, the blood crit ranges for persons who are not dehydrated range from 35%-47%.
   For bone marrow, the range is broadened to 30%-47%.
   For umbilical cord blood, the mean value is around 50%, so the lower reservoir would be larger and the top a bit smaller.

Example 2

Nail-Shaped Flexible Compartment

The "buffy area" is the possible area where the buffy coat could settle in the tube based on hematocrit of the species. Blood, marrow aspirate and umbilical cord blood buffy coat can also be referred to a concentrate meant to denote an isolation of desired cells in a smaller volume than the whole blood sample.

Cap Assembly

Apparatus with a nail-shaped flexible compartment have a cap to keep contents of internal reservoir contained and sterile. The cap can have an injection port or ports that can be used for inserting and extracting fluid. The cap can also have a filtered air vent. The cap, exoskeleton, and inner core can be held together by the cap snapping over or screwing onto the exoskeleton. The top of the inner core, the flexible compartment (see FIGS. 3A-C), has a flange that is sandwiched between the cap and the exoskeleton such that the three pieces are mated together.

Clamping

Apparatus with a nail-shaped flexible compartment are designed such that the buffy coat area can be exposed so that clamps can be applied to isolate the fractionated blood. The clamps are applied to the flattened area, where the buffy coat layer appears. The advantage of having the buffy coat layer migrate to this flattened region is that the layer, normally a very narrow layer, is broadened, thereby allowing more precise clamping, resulting in better yields and concentration of the buffy coat.

Exoskeleton

Apparatus with a nail-shaped flexible compartment are contemplated to be used with a centrifuge, and are designed with an inner core such that the buffy area of the inner core is made of flexible material. The entire inner core is completely supported during centrifugation by an exoskeleton. The exoskeleton can be partly or completely removed after centrifugation to expose the buffy coat area for clamping.

Exoskeleton Supports a Flexible Inner Core

The inner core can be made of a resilient (e.g., able to withstand relatively low g-force centrifugation) and flexible (e.g., clampable) material. The section of the inner core that is sized to capture the buffy coat is always made of a flexible material that can be clamped. The system is designed to be used point of care for use in the same patient same procedure for processing blood or marrow aspirate. The exoskeleton can be partly or completely removed to expose the clampable buffy coat area.

Figure 3B:
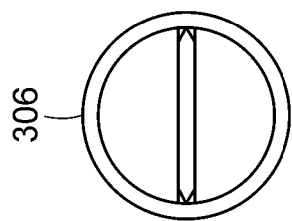
Figure 3C:
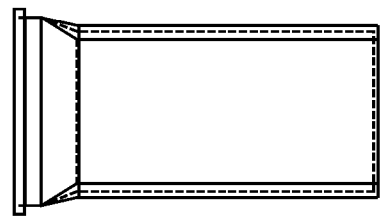
Figure 3A:
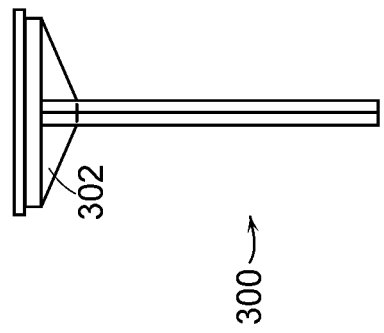
Figure 4E:
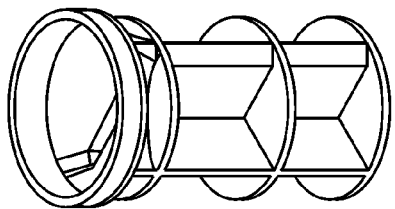
FIGS. 4A-E show different views of a rigid exoskeleton that supports a flexible compartment.
Figure 4D:
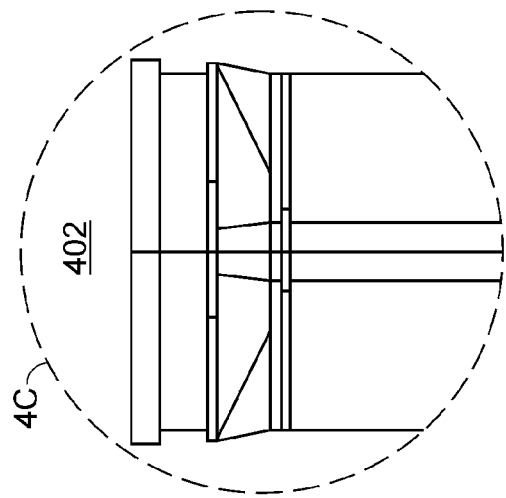
Figure 4C:
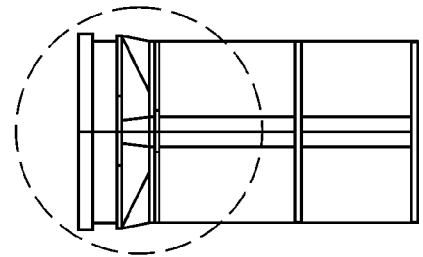
Figure 4B:
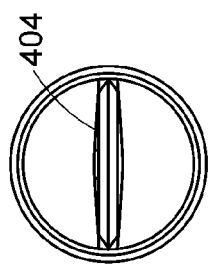
Figure 4A:
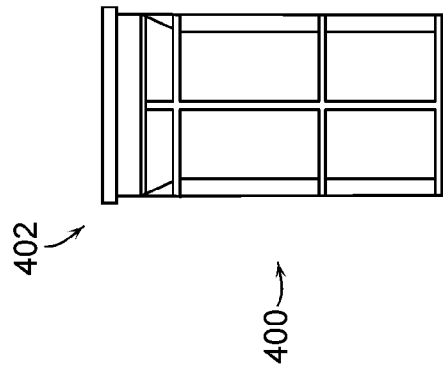

The nail-shaped inner core, as depicted in FIGS. 3A-C can be shaped like a circle on top that tapers down to a slit. The reservoirs formed by these structures have volumes based on expected fraction volumes as described in Example 1.

For samples involving umbilical cord blood, where the fractionated physiological samples are to be stored at, for example, a blood bank, the same nail-shaped flexible compartment and accompanying exoskeleton can be used, with the volumes of the reservoirs adjusted for umbilical cord samples. The system is designed to allow the collection of the blood in the birthing room and the processing of the blood at a blood bank facility (or other facility that processes and freezes umbilical cord blood for later use). The umbilical cord blood apparatus would be a larger version of point of care version, as umbilical cord blood involves larger sample volumes. The apparatus would be designed to fit in specific centrifuges that are common pieces of blood banking equipment. The upper and lower range of volumes for these samples are typically collected (60 mL to 175 mL) and ranges of hematocrit that are 40% to 60%.

Example 3

Automated Extraction

All of the apparatus are designed to have fluid extracted from injection ports at the top of the exoskeleton. This entire process can be completely automated. Any possible automated system for fluid extraction comprises 1) the cannula of the syringe to move through the injection port to above the buffy coat (either by pushing the syringe down or pushing the exoskeleton supporting the internal reservoir up relative to the cannula); 2) the movement of the plunger of the syringe back while holding the barrel of the syringe in place to create the vacuum pressure to withdraw the fluid; and 3) an optical sensor to guide the position of the cannula to allow the fractionated blood to be withdrawn in sections.

The automated steps contemplated with the current design include:

1) Inserting a cannula attached to a syringe through an injection port in the top of the disposable that is guided to the bottom of the disposable designed to hold only PPP after centrifugation and then pulling back on the plunger until all of the PPP above the bottom of the cannula has been extracted;

2) pulling apart the exoskeleton slightly to allow a set of clamps to move in and rest on top of the bottom portion of the exoskeleton;

3) pulling up the top of the exoskeleton, which also moves the flexible compartment, thereby exposing more and more of the flexible compartment until the optical sensor indicates the buffy coat rests just above the bottom of the exoskeleton. This action also moves the cannula into the slit part of the bag to a pre-determined distance above the buffy coat;

4) pulling off additional PPP;

5) moving all PPP from one syringe to another via a stop cock;

6) clamping flexible compartment;

7) extracting the buffy coat cell concentrate.

Example 4

Sterile Transfer Cannula

Umbilical cord blood banking requires a completely closed system during any processing steps. Current practice is to use blood bags and laminar hoods. Thus, in the design for umbilical cord blood, the cannula moving into the disposable cannot be exposed to air. Also, a completely closed system in the operating room may be advantageous as therapies using point of care procedures develop. To maintain a closed system, a sheath feature has been incorporated to keep the movement of the cannula into the disposable a closed system.

A tube 500 within a sheath 502 such that the tube 500 can interface with the contents of a sterile container 504 through an access port 506 on the cap 508 on one end and a luer lock 510 on the other end. The entire tube and cap assembly 512 is depicted in FIG. 6A. The tube and cap assembly can be fitted to, for example, the flexible compartment and exoskeleton of, for example, FIGS. 3-5 as shown in FIG. 1. Once assembled, the tube and cap assembly 512, along with the attached container 504 can be sterilized, noting that none of the internal contacts with a sample are exposed to a non-sterile environment (FIG. 6B). As shown in FIG. 6B, the sheath and tube can bend to the side of the container during the sedimentation, e.g., centrifugation, process for fractionating a sample. After fractionation, the tube can be fitted to an extraction device, e.g., as shown in FIG. 1 or a manual extraction device, via the luer lock fitting (FIG. 6C). The cap 5-8, is shown in FIG. 6D showing, in addition to the tube port 506, a sample injection port 514 and a filtered air vent 516. These ports allow for the sterile transfer of a physiological sample into the contained 506.

The original contents of the container, which have been transferred into the syringe, are maintained in a sterile environment. Consequently, the inner tube 500 can pass into and out of the sterile container 504 while maintaining sterility because the outer sheath 502 always protects it. The inner tube 500 and the syringe 518 become part of the sterile container because the inner tube 500 is completely enclosed. Fluid in the sterile container 506 can pass through the inner tube 500 and luer lock 510 into the syringe 518 without breaking sterility.

While this invention has been particularly shown and described with references to example embodiments thereof, it will be understood by those skilled in the art that various changes in form and details may be made therein without departing from the scope of the invention encompassed by the appended claims.

What is claimed is:

1. A method of isolating a fraction of interest from a physiological sample, comprising steps of:

providing a container comprising a plurality of reservoirs supported in a rigid exoskeleton, wherein one of said reservoirs comprises an elongated flexible reservoir which is narrower relative to at least one other reservoir;

placing a physiological fluid sample comprising a plurality of cells in said container;

separating said plurality of cells in the container into distinct relative density fractions by sedimentation;

orienting said container vertically;

exposing said elongated flexible reservoir and causing relative movement between said elongated flexible reservoir and a clamp to locate a fraction of interest among said density fractions retained in said elongated flexible reservoir;

isolating said fraction of interest retained in said elongated flexible reservoir by clamping a region of the elongated flexible reservoir adjacent the located fraction of interest; and withdrawing said fraction of interest by inserting a cannula into said elongated flexible reservoir.

2. The method of claim 1, wherein the volumes of the elongated flexible reservoir and the at least one other reservoir are selected to have the fraction of interest settle in the elongated flexible reservoir.

3. The method of claim 2, wherein the elongated flexible reservoir has a height to volume ratio that is between about 2 to about 10 times greater than the height to volume ratio of the at least one other reservoir.

4. The method of claim 2, wherein the elongated flexible reservoir has a height to volume ratio greater than about 10 times the height to volume ratio of the at least one other reservoir.

5. The method of claim 1, wherein the container comprises an upper reservoir in fluid communication with a lower reservoir, the lower reservoir being the elongated flexible reservoir.

6. The method of claim 5, wherein the lower reservoir has a height to volume ratio that is about 2 to 10 times greater than the height to volume ratio of the upper reservoir.

7. The method of claim 6, wherein the lower reservoir has a height to volume ratio that is about 3 to 4 times greater than the height to volume ratio of the upper reservoir.

8. The method of claim 7, wherein the lower reservoir has a height to volume ratio that is about 3.4 times greater than the height to volume ratio of the upper reservoir.

9. The method of claim 1, wherein the physiological sample is obtained from bone marrow aspirate, peripheral blood or umbilical cord blood.

10. The method of claim 9, wherein the fraction of interest is a buffy coat fraction.

11. The method of claim 1, further comprising isolating a second fraction of interest.

12. The method of claim 1, wherein the withdrawing step comprises withdrawing a fraction volume through the cannula.

13. The method of claim 1, wherein the volumes of the elongated flexible reservoir and exoskeleton are determined to isolate the fraction of interest in the elongated flexible reservoir.

14. The method of claim 1, wherein the withdrawing step is performed by an automated device.

15. The method of claim 1, wherein sedimentation comprises centrifugation.

16. The method of claim 1, wherein the fraction of interest is located using an optical sensor.

17. The method of claim 1, further comprising withdrawing a second fraction of interest before clamping the elongated flexible reservoir.

18. The method of claim 10, wherein the density fractions include a platelet poor plasma fraction above the buffy coat fraction, and further comprising removing platelet poor plasma with the cannula, leaving the buffy coat fraction intact.

* * * * *

UNITED STATES PATENT AND TRADEMARK OFFICE
CERTIFICATE OF CORRECTION

| | |
|---|---|
| PATENT NO. | : 8,048,678 B2 |
| APPLICATION NO. | : 12/826074 |
| DATED | : November 1, 2011 |
| INVENTOR(S) | : Duffy, Jr. et al. |

Page 1 of 1

It is certified that error appears in the above-identified patent and that said Letters Patent is hereby corrected as shown below:

On the Title page, under Related U.S. Application Data Item (63) please delete "Continuation" and insert --Division--.

In column 1, line 6, please delete "continuation" and insert --division--.

Signed and Sealed this

Thirty-first Day of January, 2012

David J. Kappos
*Director of the United States Patent and Trademark Office*